United States Patent
Zimmerling et al.

(10) Patent No.: US 8,634,909 B2
(45) Date of Patent: Jan. 21, 2014

(54) MRI-SAFE DISC MAGNET FOR IMPLANTS

(75) Inventors: Martin Zimmerling, Patsch (AT); Bernhard Jamnig, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 113 days.

(21) Appl. No.: 13/091,352

(22) Filed: Apr. 21, 2011

(65) Prior Publication Data

US 2011/0264172 A1    Oct. 27, 2011

Related U.S. Application Data

(60) Provisional application No. 61/327,158, filed on Apr. 23, 2010.

(51) Int. Cl.
*A61N 1/08* (2006.01)

(52) U.S. Cl.
USPC ............ 607/3; 607/1; 607/2; 607/60; 607/61; 607/65; 607/115; 607/116

(58) Field of Classification Search
USPC ........... 607/1–3, 9, 32–34, 55–57, 60–61, 65, 607/115, 116, 119, 124, 133
See application file for complete search history.

(56) References Cited

U.S. PATENT DOCUMENTS

| | | |
|---|---|---|
| 3,573,812 A | 4/1971 | Pihl |
| 5,877,664 A | 3/1999 | Jackson, Jr. |
| 6,178,079 B1 | 1/2001 | Renger |
| 6,178,353 B1 | 1/2001 | Griffith et al. |
| 6,190,305 B1 | 2/2001 | Ball et al. |
| 6,217,508 B1 | 4/2001 | Ball et al. |
| 6,348,070 B1 | 2/2002 | Teissl et al. |
| 6,358,281 B1 | 3/2002 | Berrang et al. |
| 6,506,987 B1 | 1/2003 | Woods |
| 6,838,963 B2 * | 1/2005 | Zimmerling et al. ......... 335/205 |

FOREIGN PATENT DOCUMENTS

| | | |
|---|---|---|
| WO | 9732629 A1 | 9/1997 |
| WO | 03092326 A1 | 11/2003 |

OTHER PUBLICATIONS

Teissl, Christian, et al "Magnetic Resonance Imaging and Cochlear Implants: Compatibility and Safety Aspects," Journal of Magnetic Resonance Imaging, Jan. 1999, vol. 9, No. 1, pp. 26-38, XP001154780.
European Patent Office, International Search Report—International Application No. PCT/IB03/02283, dated Nov. 28, 2003, 4 pages.

* cited by examiner

*Primary Examiner* — Deborah Malamud
(74) *Attorney, Agent, or Firm* — Sunstein Kann Murphy & Timbers LLP

(57) ABSTRACT

A magnetic arrangement is described for an implantable system for a recipient patient. A planar coil housing contains a signal coil for transcutaneous communication of an implant communication signal. A first attachment magnet is located within the plane of the coil housing and rotatable therein, and has a magnetic dipole parallel to the plane of the coil housing for transcutaneous magnetic interaction with a corresponding second attachment magnet.

20 Claims, 10 Drawing Sheets

(A)

(B)

(A)

(B)

(A)

(B)

(A)

(B)

MRI-SAFE DISC MAGNET FOR IMPLANTS

This application claims priority from U.S. Provisional Patent Application 61/327,158, filed Apr. 23, 2010, incorporated herein by reference.

FIELD OF THE INVENTION

The present invention relates to implantable medical devices, and specifically, to magnetic elements in such devices that allow for magnetic resonance imaging.

BACKGROUND ART

Some hearing implants such as Middle Ear Implants (MEI's) and Cochlear Implants (CI's) employ attachment magnets in the implantable part and an external part to hold the external part magnetically in place over the implant. For example, as shown in FIG. 1, a typical cochlear implant system may include an external transmitter housing 101 containing transmitting coils 102 and an external magnet 103. The external magnet 103 has a conventional coin-shape and a north-south magnetic dipole that is perpendicular to the skin of the patient to produce external magnetic field lines 104 as shown. Implanted under the patient's skin is a corresponding receiver assembly 105 having similar receiving coils 106 and an implanted internal magnet 107. The internal magnet 107 also has a coin-shape and a north-south magnetic dipole that is perpendicular to the skin of the patient to produce internal magnetic field lines 108 as shown. The internal receiver housing 105 is surgically implanted and fixed in place within the patient's body. The external transmitter housing 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction magnetization $\bar{m}$ of the implant magnet 202 is essentially perpendicular to the skin of the patient. Thus, the external magnetic field $\bar{B}$ from the MRI may create a torque $\bar{T}$ on the internal magnet 202, which may displace the internal magnet 202 or the whole implant housing 201 out of proper position. Among other things, this may damage the adjacent tissue in the patient. In addition, the external magnetic field $\bar{B}$ from the MRI may reduce or remove the magnetization $\bar{m}$ of the implant magnet 202 so that it may no longer be strong enough to hold the external transmitter housing in proper position. The implant magnet 202 may also cause imaging artifacts in the MRI image, there may be induced voltages in the receiving coil, and hearing artifacts due to the interaction of the external magnetic field $\bar{B}$ of the MRI with the implanted device. This is especially an issue with MRI field strengths exceeding 1.5 Tesla.

Thus, for existing implant systems with magnet arrangements, it is common to either not permit MRI or at most limit use of MRI to lower field strengths. Other existing solutions include use of a surgically removable magnets, spherical implant magnets (e.g. U.S. Pat. No. 7,566,296), and various ring magnet designs (e.g., U.S. Provisional Patent 61/227, 632, filed Jul. 22, 2009). Among those solutions that do not require surgery to remove the magnet, the spherical magnet design may be the most convenient and safest option for MRI removal even at very high field strengths. But the spherical magnet arrangement requires a relatively large magnet much larger than the thickness of the other components of the implant, thereby increasing the volume occupied by the implant. This in turn can create its own problems. For example, some systems, such as cochlear implants, are implanted between the skin and underlying bone. The "spherical bump" of the magnet housing therefore requires preparing a recess into the underlying bone. This is an additional step during implantation in such applications which can be very challenging or even impossible in case of very young children.

SUMMARY OF THE INVENTION

Embodiments of the present invention are directed to a magnetic arrangement for an implantable system for a recipient patient. A planar coil housing contains a signal coil for transcutaneous communication of an implant communication signal. A first attachment magnet is located within the plane of the coil housing and rotatable therein (e.g., a planar disk shape), and has a magnetic dipole parallel to the plane of the coil housing for transcutaneous magnetic interaction with a corresponding second attachment magnet.

Further specific embodiments may also have at least one magnetic focus director within the housing adjacent to the first attachment magnet and transcutaneously directing the magnetic field to increase magnetic attraction force between the first and second attachment magnets by focusing the magnetic flux (i.e. locally increasing magnetic induction). The focus director may also be used to guide magnetic field lines away from magnetically sensitive components such as implanted sensors or ferrite-based components.

The coil housing may be an implant coil housing for implantation under the skin of the patient and the signal coil would then be a receiver coil. There may also be an implant signal processor within the housing for processing the implant communication signal, and a magnetic switch within the coil housing and magnetically interacting with the first attachment magnet so as to affect operation of the signal processor as a function of magnetic orientation of the first attachment magnet. Or the coil housing may be an external coil housing for placement on the skin of the patient and the signal coil would then be a transmitter coil.

The first attachment magnet may be adapted to rotate within the coil housing in response to an external magnetic field, and there may be a lubrication coating covering at least a portion of the first attachment magnet and reducing friction between the first attachment magnet and the coil housing to promote the rotation of the first attachment magnet. At least one of the attachment magnets may have a planar disc shape, a rectangular beam shape, a cylindrical beam shape, or a cut away disc shape. Or at least one of the attachment magnets may comprise a pair of complementary cylindrical attachment magnets, which optionally may further include a magnetic flux guide connecting the pair of complementary cylindrical attachment magnets.

In any of the above, the implantable system may be a cochlear implant system, a middle ear implant system, a vestibular implant system, or a laryngeal pacemaker implant system.

DETAILED DESCRIPTION OF SPECIFIC EMBODIMENTS

Figure 1:
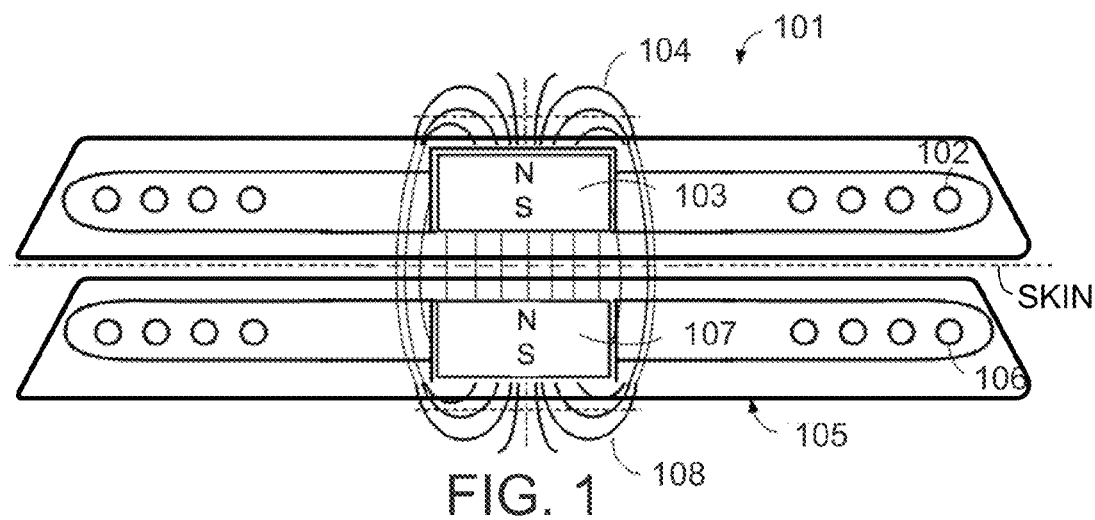
FIG. 1 shows portions of a typical cochlear implant system.
Figure 2:
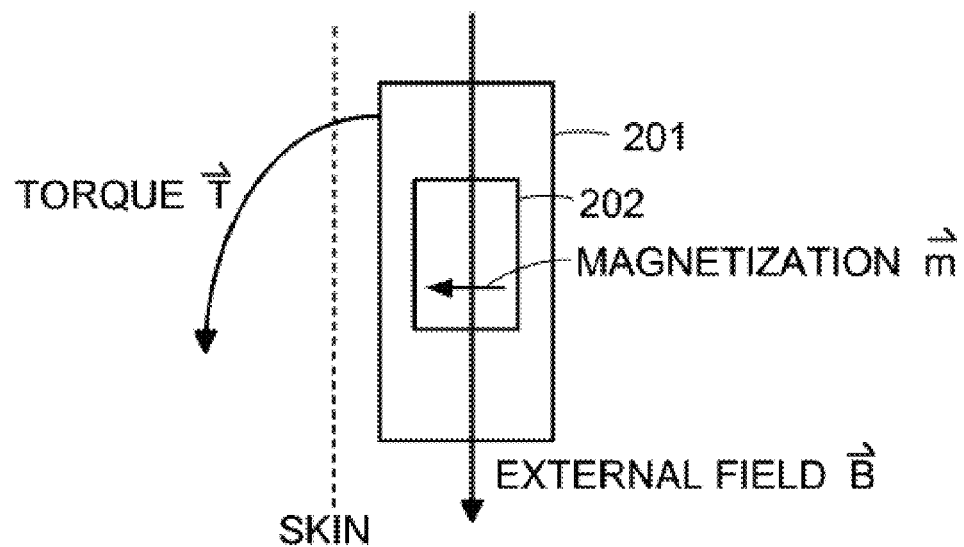
FIG. 2 illustrates the interactions that can occur between an implant magnet and the applied external magnetic field for an MRI system.
Figure 3:
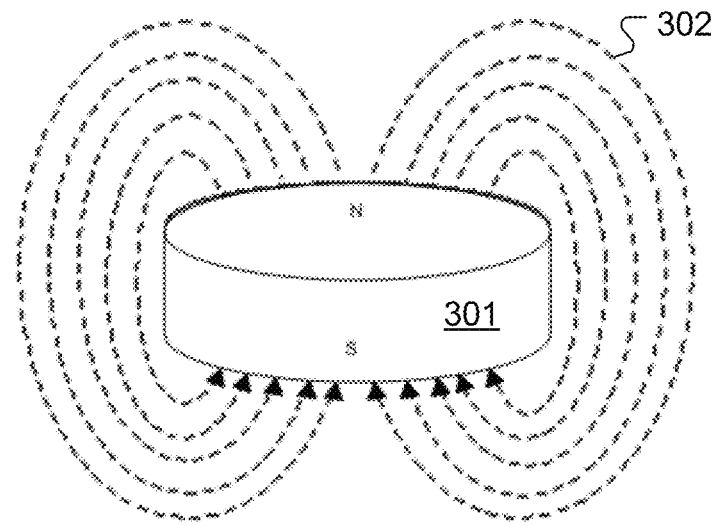
FIG. 3A-B compares the perpendicular magnetic dipole arrangement in typical existing implant attachment magnets with the parallel magnetic dipole arrangement in an attachment magnet according to an embodiment of the present invention.
Figure 3:
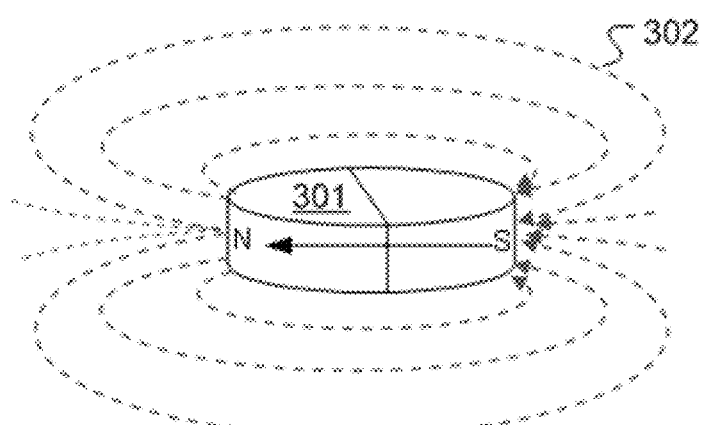

Various embodiments of the present invention are directed to a magnetic arrangement for an implantable system for a recipient patient which is compatible with MRI systems. FIG. 3A shows the magnetic field arrangement in typical existing implant attachment magnets. In this case, the attachment magnet 301 is disk-shaped (i.e., cylindrical) with the north-south magnetic dipole realized in the axial direction as is conventional producing magnetic field lines 302 as shown. Embodiments of the present invention change the direction of magnetization as shown in FIG. 3B so that the north-south magnetic dipole is oriented across the diameter of the attachment magnet 301 parallel to (i.e., "in") the plane of the coil housing, producing magnetic field lines 302 as shown.

Of course, with such an arrangement, it is important that both the internal implant receiver attachment magnet and the external transmitter attachment magnet be magnetized with the same orientation in the plane of the coil housing (i.e., parallel to the skin). Then when the external coil housing is placed onto the patient's skin over the implant coil housing, the two attachment magnets turns around on their axis such that the north and south poles of one attachment magnet are positioned adjacent to south and north poles respectively of the other attachment magnet thereby maximizing the attractive magnetic force between the two.

Figure 4:
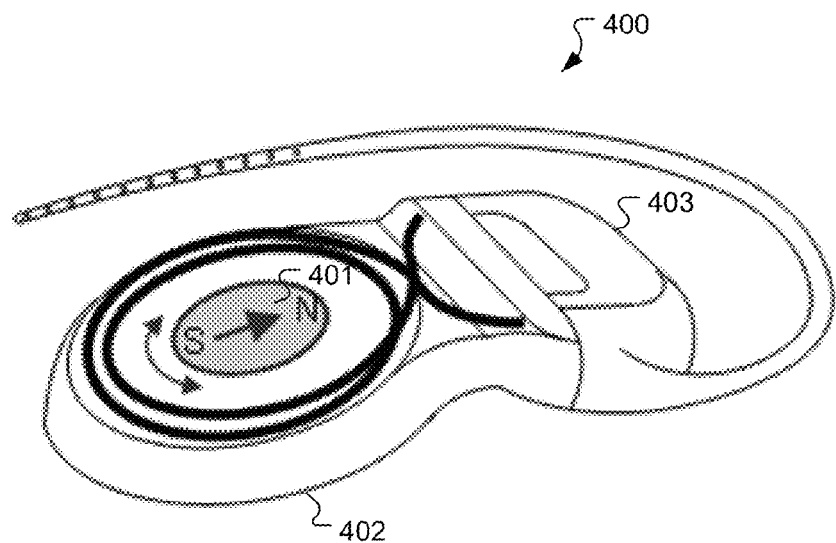
FIG. 4A-B show elevated perspective and side cross-sectional views of a cochlear implant coil housing having an attachment magnet according to an embodiment of the present invention.
Figure 4:
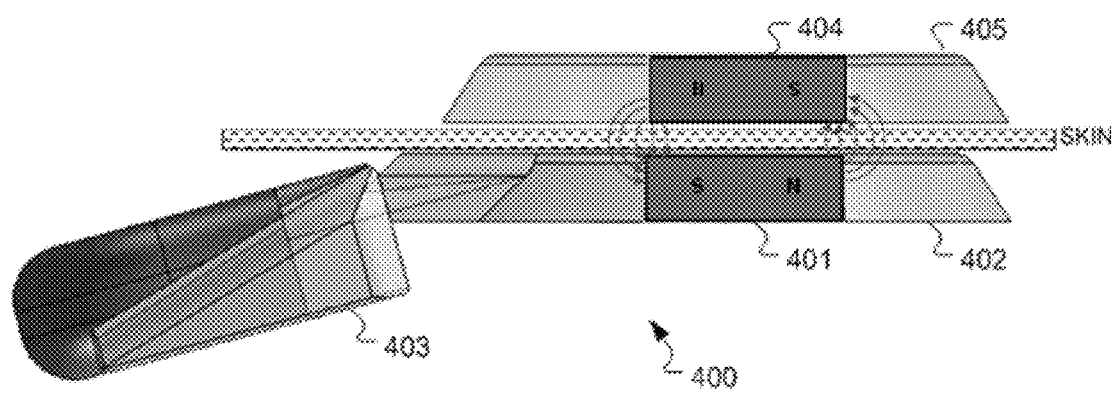

FIG. 4A shows an elevated perspective view and FIG. 4B shows a side cross-sectional view of a cochlear implant 400 having a planar coil housing 402 that contains a signal coil for transcutaneous communication of an implant communication signal. A first attachment magnet 401 is located within the plane of the coil housing 402 and rotatable therein (e.g., a planar disk shape) has a magnetization direction with a magnetic dipole parallel to the plane of the coil housing 402. An external transmitter coil housing 405 with a corresponding second attachment magnet 404 with a similar magnetic dipole direction parallel to the plane of its coil housing 405 so that when placed on the skin of the recipient patient, their respective magnetic fields cause the two attachment magnets 401 and 404 to self-orient as described above to form a magnetic attraction connection between them. In specific embodiments, the coil housing 402 may be made have a titanium case with the attachment magnet 401 located outside the titanium case, for example, embedded in a silicone coil assembly. Alternatively, the coil housing 402 may be a ceramic case where the attachment magnet 401 is hermetically encapsulated within the ceramic housing.

Figure 5:
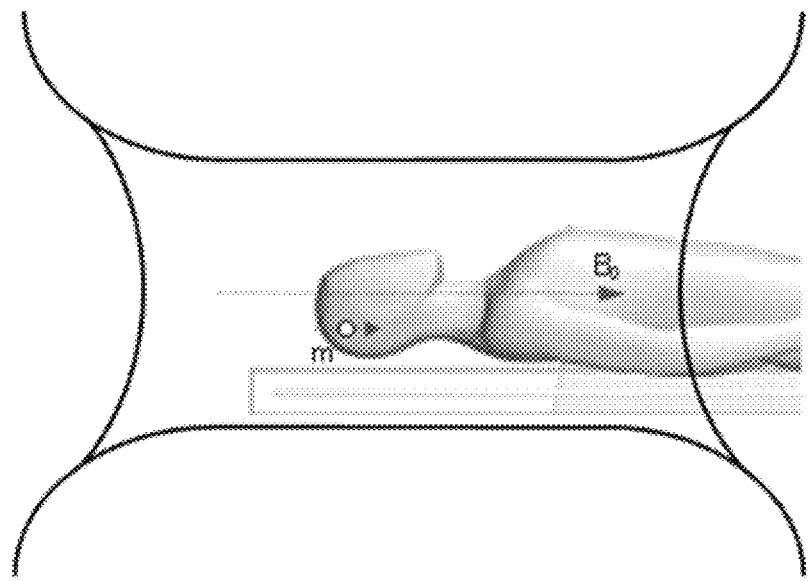
FIG. 5 shows a patient in a typical closed MR scanner where the main magnetic field goes from head to toe on the patient.
Figure 6:
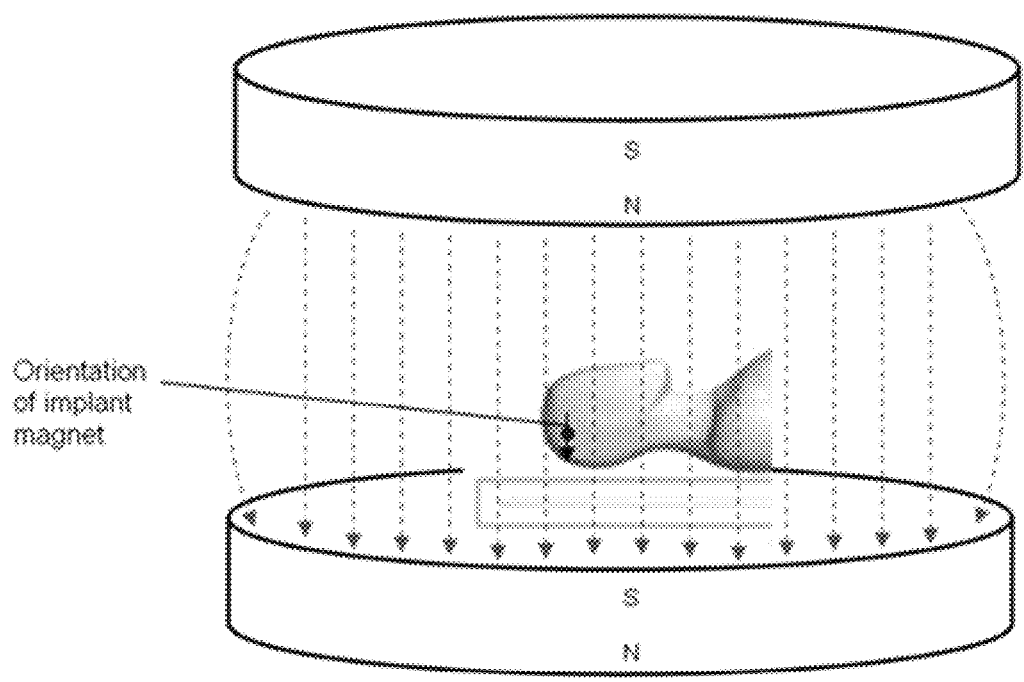
FIG. 6 shows a patient in a typical open MR scanner where the main magnetic field goes from front to back on the patient.

When a person wearing an implant with such an attachment magnet needs to undergo an MRI, they can enter the scanner room after the external components of the implant system have been removed. As the implant user is brought into the MR scanner, the attachment magnet may have a component of its magnetization which is perpendicular to the external magnetic field of the MR scanner. This will result in the attachment magnet turning around on its axis to align the magnetization direction of its magnetic dipole with the static field of the MR scanner. This occurs in both conventional closed MR scanners characterized by a bore with a horizontal static magnetic field as shown in FIG. 5 running parallel to the body axis from head to toe on the patient, as well as in so-called open MR scanners as shown in FIG. 6 characterized by a vertical static magnetic field running perpendicular to the body axis through the body of the patient from front to back.

Figure 7:
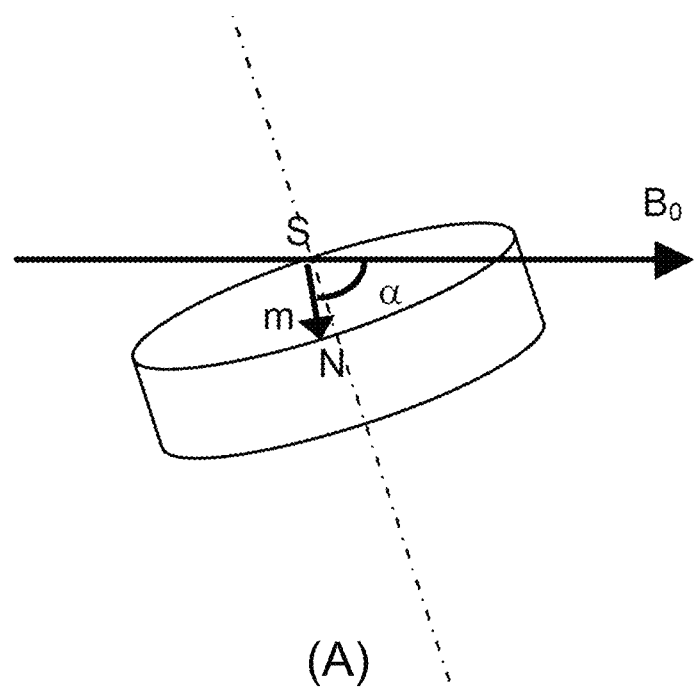
FIG. 7 A-B shows the case where the magnetization direction of the attachment magnet is not perpendicular to the main external MRI field.
Figure 7:
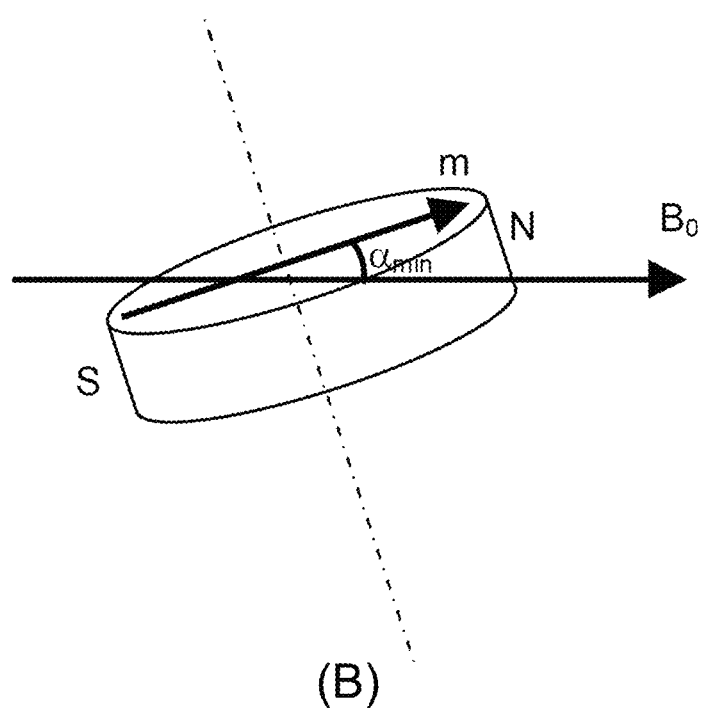

When the attachment magnet of the implant can align with the static magnetic field of the MR system, there is no torque exerted by the static magnetic field of the MR on the attachment magnet/coil housing arrangement, nor is the magnetic force of the attachment magnet weakened. This is also the case when the attachment magnet cannot align completely with the static magnetic field of the MR scanner, but remains at an angle up to about 20° between the magnetic momentum of the implant magnet and the static magnetic field of the MR scanner. Since the torque is proportional to the sine of the angle, for example, the torque is reduced for a remaining angle of 20° to about ⅓ (66% reduction) of the torque when the attachment magnet remains fixed at the worst case angle of 90°. In situations where the rotational axis of the attachment magnet (i.e., its axis of symmetry) is exactly perpendicular to the static magnetic field of the MR system, the attachment magnet can turn around and can align its magnetic dipole m exactly with the static magnetic field $B_0$ without torque or demagnetization. But this is an ideal theoretical case, in most real situations the rotational axis of the attachment magnet is just close to but not exactly perpendicular to the static magnetic field, e.g., at an angle of 70° or 80° instead of 90°. This is shown in FIG. 7A. The attachment magnet will turn around on its axis and will try to align its magnetic dipole m with the surrounding magnetic field $B_0$ as best possible (FIG. 7B). There will remain a small angle ($\alpha_2$), and the residual torque is proportional to the sine of this angle (e.g. torque is only about ⅓ when the remaining angle is of 20°). Since the remaining angle typically is small(<<90° there is virtually no risk for an attachment magnet weakening even for high values of $B_0$ (>1.5 Tesla). It will only be when (or if) the rotational axis of the attachment magnet is (almost) parallel to the static magnetic field $B_0$ of the MR system (as in the prior art) that the attachment magnet would then have a magnetic dipole which is essentially perpendicular to $B_0$ (regardless of how the magnet turns around), and the full torque and risk of magnet weakening would be present.

Figure 8:
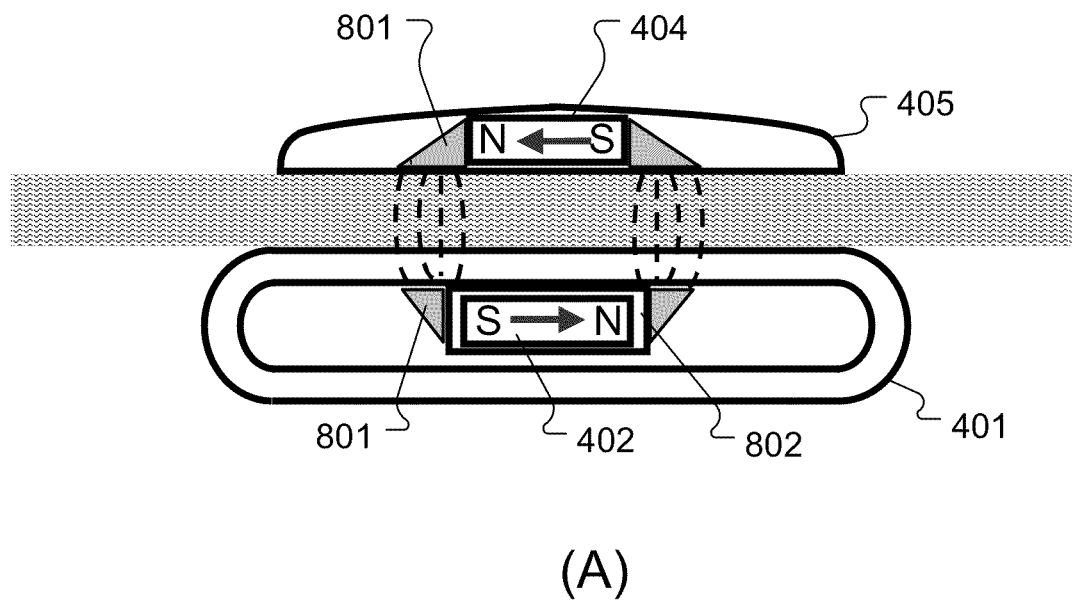
FIG. 8 A-B shows side and top view structural details of an embodiment having a soft magnetic focus director arrangement.
Figure 8:
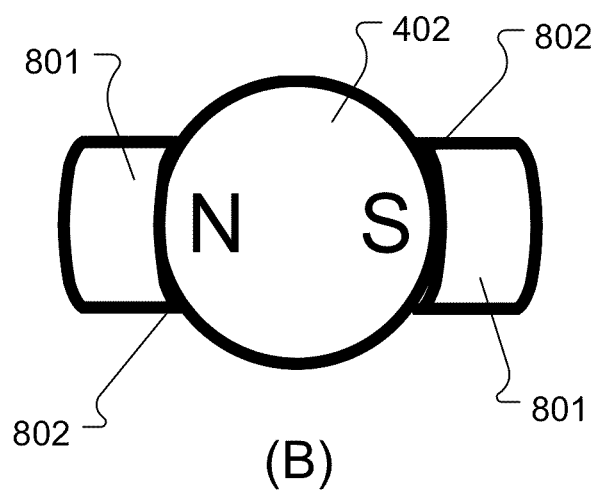

FIG. 8 A-B shows side and top view structural details of an embodiment wherein the coil housing 401 also contains a magnetic focus director 801 which surrounds some or all of the attachment magnet 402. The magnetic focus director 801 is made of a soft ferromagnetic material that directs the magnetic field of the attachment magnet 402 through the skin to increase the magnetic attraction force with the other corresponding attachment magnet by focusing the magnetic flux (i.e. locally increasing magnetic induction). The focus director 801 may also be used to guide magnetic field lines away from magnetically sensitive components such as implanted sensors or ferrite-based components. In the specific embodiment shown in FIG. 8 A-B, the magnetic focus director 801 has two generally rectangular opposing director pieces located on opposite sides of the attachment magnet 402 which then may have a defined equilibrium position in the absence of an external magnetic field such as an MRI field. The embodiment shown in FIG. 8 also shows a lubrication coating 802 made of polytetrafluoroethylene (PTFE) that covers at least a portion of the attachment magnet 402 and reduces the friction between the attachment magnet 402 and the coil housing 401 so as to promote the rotation of the attachment magnet 402 in response to external magnetic fields.

In some embodiments, the attachment magnet may be fixed within the external component (e.g., transmitter coil housing) to prevent its rotation. For example, the external attachment magnet may be fixed within the external component so that its magnetic axis is in a well-defined orientation when the external component is worn on the body. The position of the external component can then adjusted for the best magnet orientation to achieve the optimal (maximum) magnetic fixation of the external component.

Alternatively, the attachment magnet may be encapsulated within the external component so that it can rotate on its axis like the attachment magnet in the implant. In some hybrid embodiments, the implant attachment magnet may be not completely free to turn around, but may be limited to a certain maximum rotation angle. When both the internal and the external attachment magnets are free to rotate, if at least one of the attachment magnets has its center of gravity offset from its rotational axis, then that magnet will turn around when the implant user turns around relative to the magnet axis. Since both attachment magnets are magnetically coupled, the implant attachment magnet will also turn around. Based on this arrangement, a (one-axis) gyro sensor could be implemented, for example, for an electronic vestibular prosthesis. In a different embodiment, the implant attachment magnet may have a restoring force which positions it into a defined orientation as long as no external magnetic field is present.

Figure 9:
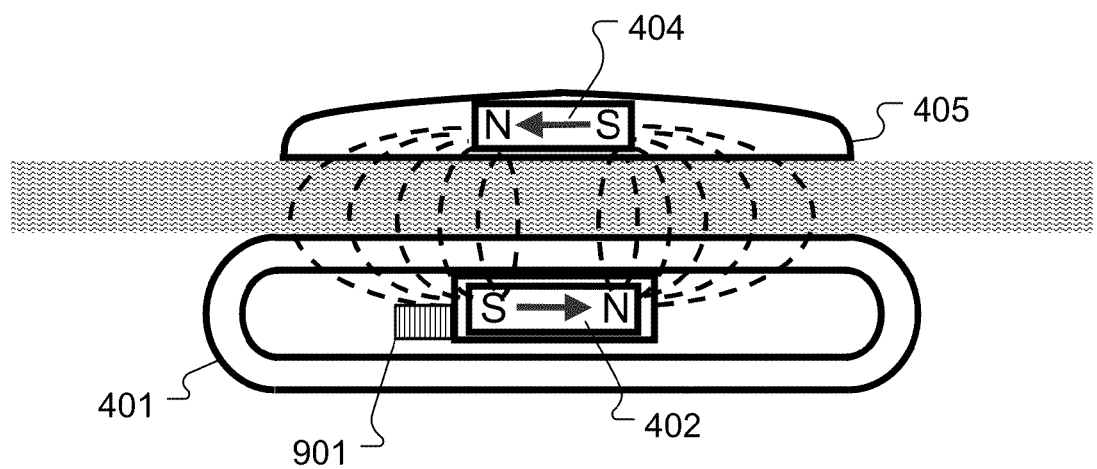
FIG. 9 shows an embodiment having a magnetic switching arrangement having a switching operation which is a function of the orientation of the attachment magnet.

FIG. 9 shows an embodiment which includes a magnetic switch 901 within the coil housing 401. The magnetic switch 901 magnetically interacts with the attachment magnet 402 so as to affect the operation of the implant signal processor as a function of the orientation of the attachment magnet 402. For example, with the south pole of the attachment magnet 402 facing downwards (caudally) indicates that an external transmitter coil is located over the coil housing 401 so the implant signal processor is activated. On the other hand, reorienting the attachment magnet 402 so that the north magnetic pole faces downwards could trigger a different operating mode, e.g., a telemetry mode, recharging or programming mode, or for activating/deactivating electrodes. Such functionality would require that the external attachment magnet be fixed within its housing to prevent its rotation.

Figure 10:
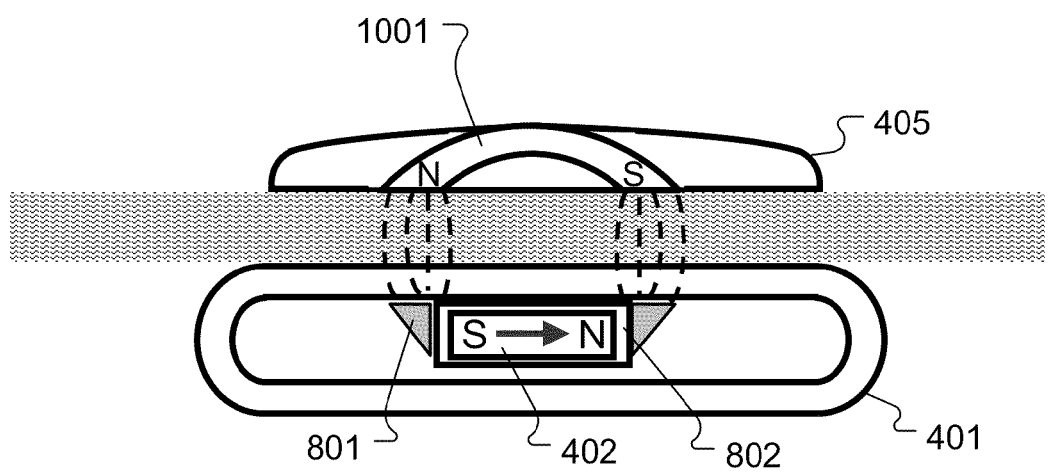
FIG. 10 shows an embodiment similar to the one in FIG. 8 which includes use of a horseshoe shaped magnet.

It is worth noting that while the embodiments described above are disk shaped (cylindrical), but that is not necessarily required. Rather, any shape could be implemented so long as the magnetization is parallel to the coil housing and the skin. For example, FIG. 10 shows an embodiment similar to the one in FIG. 8 which includes use of a horseshoe shaped attachment magnet 1001. In addition, in the embodiments described above, the attachment magnets have a magnetization axis that perpendicular to the rotational axis of the disk, but in other embodiments, the attachment magnets may more generally have a magnetization axis that is not parallel to the rotational axis.

Figure 11:
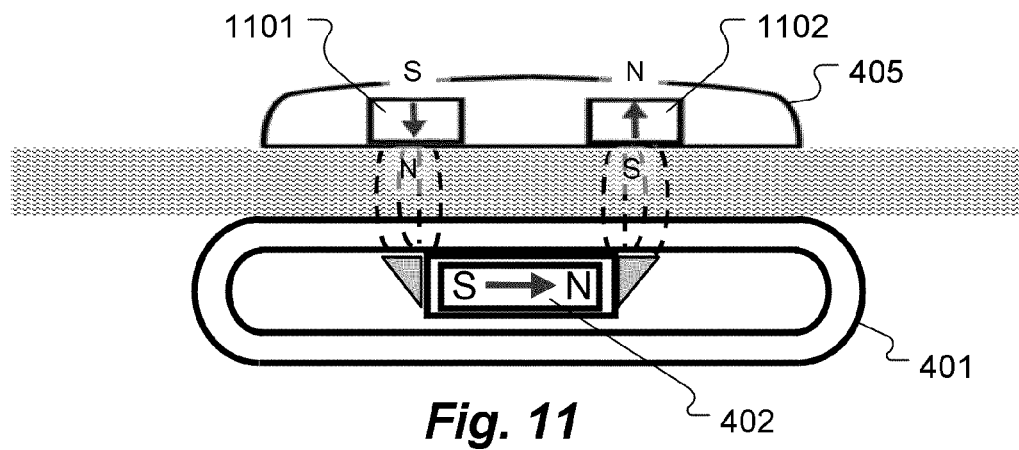
FIG. 11 shows a side view of an embodiment having two corresponding cylindrical external attachment magnets.
Figure 12:
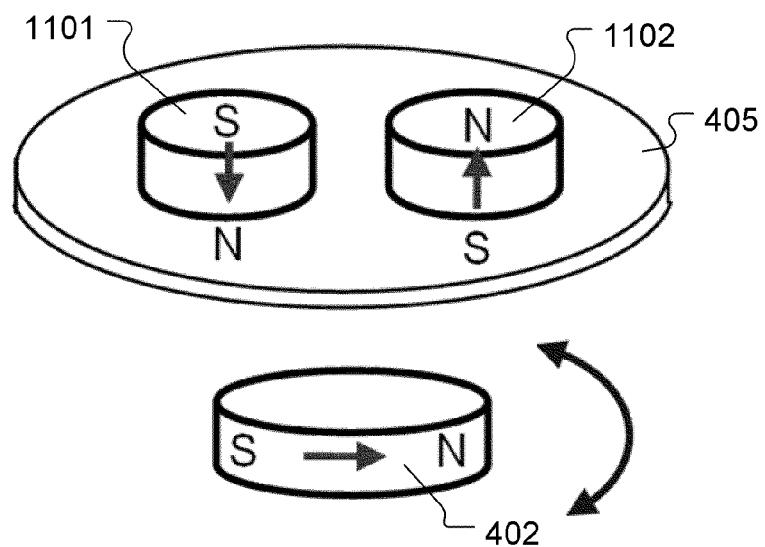
FIG. 12 shows an elevated perspective view of some of the same structures as in FIG. 11.
Figure 13:
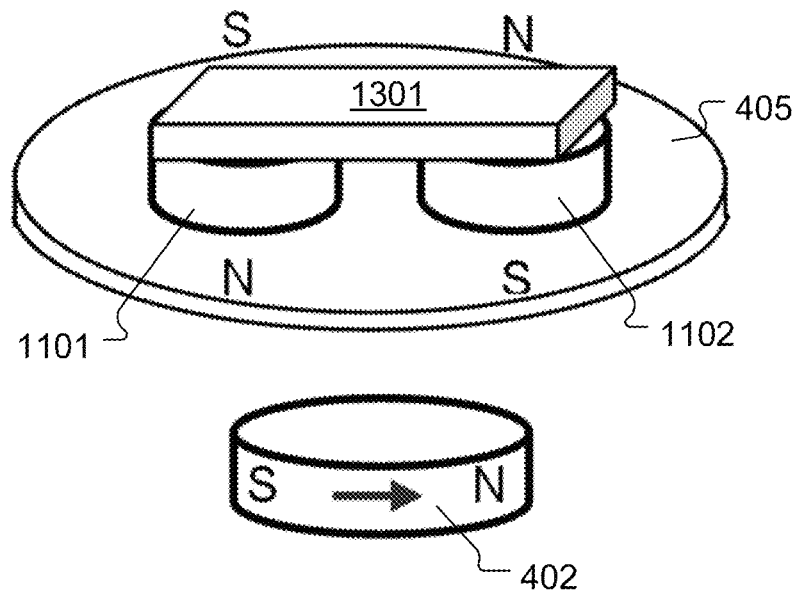
FIG. 13 shows a similar arrangement with an additional magnetic flux guide.

FIG. 11 shows a side view of another embodiment wherein the external coil housing 405 contains a pair of complementary cylindrical attachment magnets 1101 and 1102 with opposite magnetic polarities as shown which interact with the single cylindrical implant attachment magnet 402 which is free to rotate in the plane of the implant housing 405 to orient itself to magnetically interact with the external attachment magnets 1101 and 1102. FIG. 12 shows an elevated perspective view of some of the same structures. FIG. 13 shows a similar arrangement with an additional magnetic flux guide 1301 connecting the two external attachment magnets 1101 and 1102.

Figure 14:
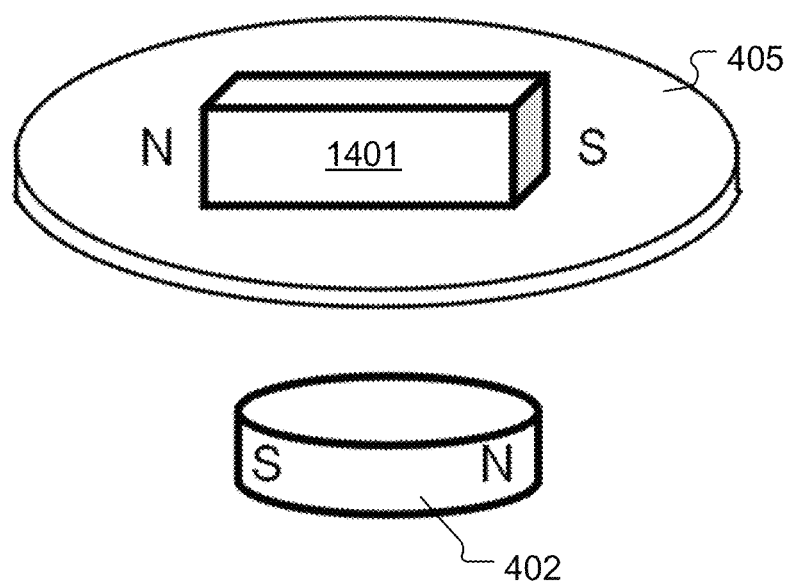
FIG. 14 shows an embodiment having an external attachment magnet with a rectangular beam shape.
Figure 15:
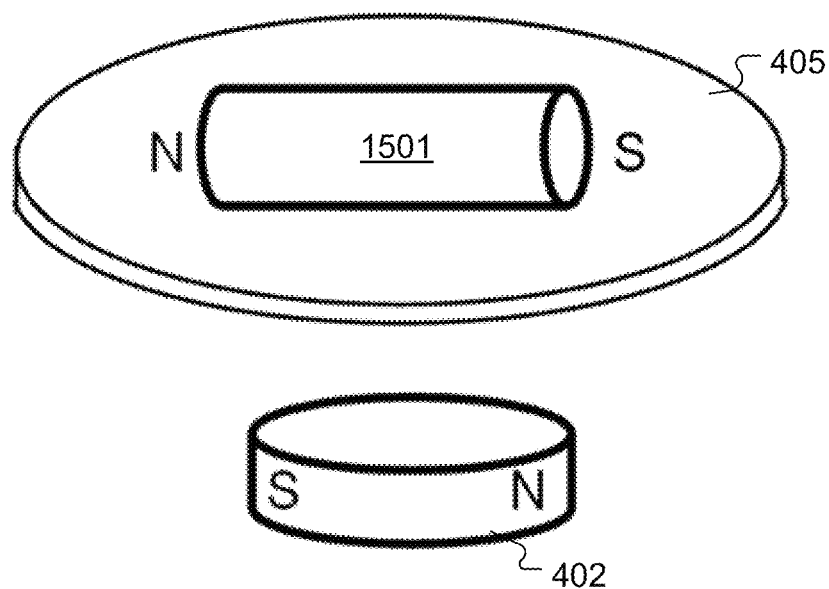
FIG. 15 shows an embodiment having an external attachment magnet with a cylindrical beam shape.
Figure 16:
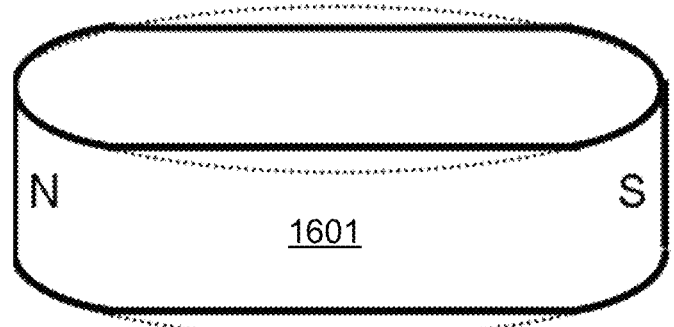
FIG. 16 shows an embodiment having an external attachment magnet based on a disc shape with the less magnetic regions cut away.

FIG. 14 shows an embodiment having an external attachment magnet 1401 with a rectangular beam shape. FIG. 15 shows an embodiment having an external attachment magnet 1501 with a cylindrical beam shape. FIG. 16 shows an embodiment having an external attachment magnet 1601 based on a disc shape with the less magnetic regions cut away to save weight and volume without significantly compromising overall magnetic field strength.

Optimizing the external attachment magnet arrangement minimizes the total mass and controls the spatial distribution of the magnetic field, which in turn can influence the electronic circuitry related to the external coil—e.g., reduced influence of the external attachment magnets on the inductive signal transmission properties. In addition, properly optimized design of the external attachment magnet can offer improved magnetic field distance characteristics, e.g., allowing a shallower field. Some embodiments may have similar implant attachment magnet arrangements.

Non-spherical shaped magnets with a magnet field oriented in the plane of the coil housing (i.e., parallel to the skin) basically the same advantages with regards to MR systems as with spherical magnet designs, with the main limitation being that the disk-shape attachment magnet design described above allows for rotation of the magnet in only one plane. Still when the implant is placed inside the body in a sagittal plane orientation (as with a hearing implant) and with a standard MRI examination position of the patient (i.e. in supine position with the head kept straight), the implant attachment magnet can align quite well with the static magnetic field both in closed MR scanners (with a horizontal main magnetic field) as well as is open MR scanners (with the main magnetic field in vertical direction).

Attachment magnets according to embodiments of the present invention present a slim profile which is safe for MRI field strengths up to and beyond 3 Tesla without the need to surgically remove the implant magnet. Alternatively, in some embodiments the implant attachment magnet may be adapted to be temporarily removable by minor surgery from the implant coil housing if desired to reduce MRI artifacts.

In contrast to spherical design attachment magnets, the present coil housing can have a flat bottom so that there is no need to drill a recess into the bone during implantation of the device. This makes such a magnet design especially well-suited for implantation in young children. Moreover, embodiments can be equally effective where there is a relatively large magnet in the implanted part and a relatively small magnet in the external part, and vice versa. And due to the different magnetization direction, it is expected that the MR imaging artifact may be smaller compared to conventional implant magnets, for example, extending less in the medial direction.

Compared to the conventional disk magnet concept with axial magnetization, embodiments of the present invention have attractive forces on both poles, and the attraction is caused by two forces which apply at the two poles of each magnet. The result is that the shear force between the external attachment magnet and the implant attachment magnet is higher in the direction of the magnetization axis of the two magnets. By turning the external attachment magnet for optimal orientation over the implant (e.g. vertical magnetic axis), a better magnetic attachment of the external parts can be achieved. In such an arrangement, the external attachment magnet also stays in place over the implant attachment magnet with less lateral displacement even in response to small mechanical shocks. The present embodiments also have a better (shallower) force-over-distance diagram than two conventional magnets with axial magnetization. It may be advantageous if the attractive force does not vary greatly over the distance between the two attachment magnets.

With standard supine patient position where the implant attachment magnet is oriented in a coronal plane, embodiments of the attachment magnet described here can align well with the static magnetic field in closed MR scanners only while such an implant magnet in axial orientation would only align with the static magnetic field in open scanners with vertical magnetic field. The torque exerted to the implant can remain relatively high when the implant magnet which has only one degree of freedom cannot align well enough with the external magnetic field.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable system for a recipient patient, the implantable system comprising:
   a coil housing configured to be implanted under the patient's skin, the coil housing having a planar outer surface configured to lie parallel to the patient's skin and containing a signal coil for transcutaneous communication of an implant communication signal; and
   a planar disc shaped first attachment magnet within the coil housing, the first attachment magnet adapted to be rotatable therein, having a magnetic dipole moment oriented across a diameter of the first attachment magnet, and configured within the coil housing such that the magnetic dipole moment remains substantially parallel to the planar outer surface of the coil housing when the first attachment magnet rotates for transcutaneous magnetic interaction with a corresponding second attachment magnet.

2. An implantable system according to claim 1, further comprising:
   at least one magnetic focus director within the housing laterally adjacent to the first attachment magnet and transcutaneously directing the magnetic field to increase magnetic attraction force between the first and second attachment magnets.

3. An implantable system according to claim 1, wherein the signal coil is a receiver coil.

4. An implantable system according to claim 3, further comprising:
   an implant signal processor within the housing for processing the implant communication signal; and
   a magnetic switch within the coil housing configured to magnetically interact with the first attachment magnet so as to affect operation of the signal processor as a function of magnetic dipole moment orientation of the first attachment magnet.

5. An implantable system according to claim1, further comprising:
   a lubrication coating covering at least a portion of the first attachment magnet and configured to reduce friction between the first attachment magnet and the coil housing to promote the rotation of the first attachment magnet.

6. An implantable system according to claim 1, wherein the implantable system is a cochlear implant system.

7. An implantable system according to claim 1, wherein the implantable system is a middle ear implant system.

8. An implantable system according to claim 1, wherein the implantable system is a vestibular implant system.

9. An implantable system according to claim 1, wherein the implantable system is a laryngeal pacemaker implant system.

10. An implant system comprising:
    an implantable system comprising:
       a coil housing configured to be implanted under the patient's skin, the coil housing having a planar outer surface configured to lie parallel to the patient's skin and containing a signal coil for transcutaneous communication of an implant communication signal; and
       a planar disc shaped first attachment magnet within the coil housing, the first attachment magnet adapted to be rotatable therein, having a magnetic dipole moment oriented across a diameter of the first attachment magnet, and configured within the coil housing such that the magnetic dipole moment remains substantially parallel to the planar outer surface of the coil housing when the first attachment magnet rotates for transcutaneous magnetic interaction with a corresponding second attachment magnet; and
    an external device comprising:
       a transmitter housing containing a second attachment magnet configured to hold the external device in place over the implantable system on the patient's skin.

11. An implant system according to claim 10, wherein the second attachment magnet has a magnetic dipole moment and the transmitter housing includes a planar outer surface configured to lie parallel to the patient's skin, the second attachment magnet configured within the transmitter housing such that the magnetic dipole moment of the second attachment magnet is parallel to the planar outer surface of the transmitter housing.

12. An implant system according to claim 10, further comprising:
    at least one magnetic focus director within the coil housing laterally adjacent to the first attachment magnet and transcutaneously directing the magnetic field to increase magnetic attraction force between the first and second attachment magnets.

13. An implant system according to claim 12, further comprising:
    at least one magnetic focus director within the transmitter housing laterally adjacent to the second attachment magnet and transcutaneously directing the magnetic field to increase magnetic attraction force between the first and second attachment magnets.

14. An implant system according to claim 10, wherein the second attachment magnet has a planar disc shape.

15. An implant system according to claim 10, wherein the second attachment magnet has a rectangular beam shape.

16. An implant system according to claim 10, wherein the second attachment magnet has a cylindrical beam shape.

17. An implant system according to claim 10, wherein the second attachment magnet has a cut away disc shape.

18. An implant system according to claim 10, wherein the second attachment magnet comprises a pair of complementary cylindrical attachment magnets.

19. An implant system according to claim 18, further comprising:
    a magnetic flux guide connecting the pair of complementary cylindrical attachment magnets.

20. An implant system according to claim 10, wherein the transmitter housing contains transmitting coils configured to interact with the signal coil.

* * * * *